(12) United States Patent
Smith

(10) Patent No.: US 7,687,040 B2
(45) Date of Patent: Mar. 30, 2010

(54) AUTOMATED PORTABLE AND SUBMERSIBLE OZONE GENERATOR

(76) Inventor: Rod A. Smith, 10225 No. Oak Creek La., Highland, UT (US) 54003

( * ) Notice: Subject to any disclaimer, the term of this patent is extended or adjusted under 35 U.S.C. 154(b) by 463 days.

(21) Appl. No.: 11/056,026

(22) Filed: Feb. 11, 2005

(65) Prior Publication Data

US 2005/0284745 A1 Dec. 29, 2005

Related U.S. Application Data

(60) Provisional application No. 60/543,630, filed on Feb. 11, 2004, provisional application No. 60/618,851, filed on Oct. 14, 2004.

(51) Int. Cl.
*B01J 19/08* (2006.01)
(52) U.S. Cl. ............... 422/186.12; 204/176; 210/760
(58) Field of Classification Search ........... 422/186.07, 422/186.12, 121; 204/176; 210/760
See application file for complete search history.

(56) References Cited

U.S. PATENT DOCUMENTS

| | | | |
|---|---|---|---|
| 1,056,789 A | 3/1913 | Held | |
| 1,971,513 A | 8/1934 | Stoddard | 204/32 |
| 2,744,865 A | 5/1956 | Penning | 204/319 |
| 3,215,616 A | 11/1965 | Spielman | 204/313 |
| 5,087,426 A * | 2/1992 | Inoue et al. | 422/123 |
| RE34,571 E | 3/1994 | Uys | 422/186.07 |
| 5,501,844 A | 3/1996 | Kasting, Jr. et al. | 422/186.15 |
| 5,508,008 A | 4/1996 | Wasser | 422/186 |
| 5,514,345 A | 5/1996 | Garbutt et al. | 422/124 |
| 5,681,533 A | 10/1997 | Hiromi | 422/121 |
| 5,702,507 A | 12/1997 | Wang | 96/55 |
| 5,975,090 A * | 11/1999 | Taylor et al. | 132/116 |
| 6,066,348 A | 5/2000 | Yuan et al. | 426/236 |
| 6,120,739 A | 9/2000 | Thomas et al. | 422/186.07 |
| 6,156,268 A | 12/2000 | Curry et al. | 422/4 |
| 6,294,211 B1 | 9/2001 | Yuan et al. | 426/235 |
| 6,447,731 B1 | 9/2002 | Sun et al. | 422/121 |
| 6,503,547 B1 | 1/2003 | Lima | 426/231 |
| 6,599,486 B1 | 7/2003 | Borgstrom | 422/186.07 |
| 6,632,407 B1 * | 10/2003 | Lau et al. | 422/186 |

OTHER PUBLICATIONS

Negative Ion Generators, Web pages, http://www.negativeiongenerators.com, Feb. 11, 2005.
Advanced Air Purifier, Web pages, http://www.advancedairpurifier.com, Mar. 16, 2004.
Negative Ion Generators and Mini Air Ionizer, Web Pages, http://www.attf.com, Mar. 16, 2004.
Heaven Fresh, web pages, http://www.heavenfresch.com, Mar. 16, 2004.
Hepalta Purified Air, web pages, http://www.hepalta.com, Mar. 16, 2004.

* cited by examiner

*Primary Examiner*—Kishor Mayekar
(74) *Attorney, Agent, or Firm*—Todd E. Zenger; Kirton & McConkie

(57) ABSTRACT

The present invention is directed to a portable ozone generator for use in small, confined, uninhabited spaces, such as refrigerators. The generator has a clam shell top and bottom. The bottom is of unitary construction and houses batteries. The top house electrical components, including circuitry for time generation of ozone.

15 Claims, 8 Drawing Sheets

AUTOMATED PORTABLE AND SUBMERSIBLE OZONE GENERATOR

RELATED APPLICATION

This claims priority to pending provisional patent application Ser. No. 60/543,630 filed Feb. 11, 2004 and continuation-in-part of provisional patent applications Ser. No. 60/618,851 filed Oct. 14, 2004.

BACKGROUND OF THE INVENTION

1. Field of the Invention

The present invention relates to ozone generators for use in an uninhabited space, in particular, a self-contained, portable ozone generator to treat air. In particular, the present invention relates to systems and methods for devices used to eliminate bacteria and odor inside a home refrigerator.

2. Background and Related Art

Many air treatment devices have been developed. Among current existing techniques, some use activated carbon to eliminate odor. Using activated carbon to eliminate odor requires frequent replacements, which causes inconvenience. Moreover, activated carbon methods have no germs-killing function.

A number of ozone generators have been developed for industrial, commercial and other uses. Examples include U.S. Pat. Nos. 6,652,816, 6,599,486, 6,503,547, 6,447,731, 6,294,211, 6,156,268, 6,066,348, 5,702,507, 5,681,533, 5,514,345, 5,508,008, 5,087,426, 3,215,616, 2,744,865, 1,971,513, 1,056,789, and RE 34,571.

In addition, commercial devices such as the Neo-Tec® XJ-600 car ionizer and XJ-100 refrigerator ionizer have been marketed. The XJ-100 is not designed for use in wet environments. It automatically runs every hour and has a three setting HI-LO-OFF switch, which may be elected by the user to control the operation of the device.

SUMMARY AND OBJECTS OF THE INVENTION

The present invention is directed to a compact, portable and partially submersible ozone generator for use in uninhabited spaces. The generator can be used in refrigerators or other storage spaces to inhibit decomposition of foods. Such generators can also be used to defeat or minimize noxious odors in places like lockers, coolers, garbage areas, automobiles, and other uninhabited areas where undesirable odors are present.

The ozone generator in the present invention is compact in that its physical dimensions are approximately six inches high, five inches wide, and three inches deep. This permits the generator to be used in small spaces. Another benefit of its compact size is that the generator uses little space in, for example, a refrigerator, cooler, or other food storage container.

The ozone generator of the present invention is portable in that it does not require a plug or outlet, but is in one embodiment operated by batteries.

In a first embodiment it is operated by four size D batteries. It is also contemplated that portability would be accomplished with a custom lithium battery or with the ability to plug the unit into a cigarette lighter-type electrical source.

The ozone generator of the present invention is semi-submersible. That is, it comprises a lower and upper shell portion. The lower shell portion projects upward about three inches up to the point of joining with the upper shell portion. The device is, therefore, capable of being submersed in or stand in liquids because the base portion is waterproof.

Other features of the ozone generator of the present invention includes a base portion which houses the batteries. Placing the batteries in the base gives the base weight and stabilizes the device.

The second or upper shell portion attaches to the base shell portion. Attached to the upper shell portion is a circuit board to control the device. The upper shell includes a housing to receive an upper platform spaced from the circuit board. The upper platform hosts a fan which draws air into the upper shell through an intake vent and drives the air upward past an ozone emitter or generator element. In this way, the ozone generator forces air circulation through the device and facilitates circulation of ozone in the container in which the ozone generator is placed.

The upper shell also houses an energy converter, if needed. The converter converts battery power into the electrical power needed to run the ozone generator.

Electrical circuitry is also provided to perform a number of functions including a timing device to automatically turn the ozone generator on and off at desired intervals or when the level of ozone in the container drops below a desired level. A preferred interval is to have the ozone generator run for two minutes in each fifty (50) minute period. Ideally the device of the present invention services up to a sixteen cubic foot container or uninhabited space.

The electrical circuitry also controls an LED indicator light on the face of the ozone generator. The LED has three primary indicators. It is green when the ozone generator is on during one of its two-minute ozone generation cycles. The LED is not illuminated when the ozone generator is not generating ozone. And the LED illuminates red in a low battery condition.

The electrical circuitry also controls the flow of energy from the batteries to the converter. A particular feature of this ozone generator is that there is no on/off switch either interior or exterior on the device. As soon as the top shell is attached to the bottom shell member, contacts connected to the top shell complete the electrical circuit, and the device goes into automatic operation mode requiring no user selection.

To further prevent any corrosion or shorting of the electronic circuitry, all electrical components are rubber or waterproof coated or covered in a waterproof box wherever possible.

The ozone generator of the present invention utilizes known corona discharge ozone generator structure and function; utilizing a light blue rod and circled about by wire mesh.

Similarly, the electrical converter can be a known device to convert battery energy to the energy needed to operate the ozone generator to create ozone.

Another feature of the device is that the screened mesh at the top of the upper shell through which air is blown by the fan is preferably made of stainless steel to prevent any oxidation by the O3 generated by the ozone generator.

One embodiment is specifically designed for use in a home refrigerator. The device works through timed control of circuit and high-voltage electricity. It has the same general structural features as discussed above. The refrigerator device comprises, however, a small physical size consistent with the limited space interior of a refrigerator.

Under operation, transformers generate a high voltage of several thousand volts of electricity. To generate ozone, one end of the high voltage is connected through wires and needles as described below. Since ozone has a high oxidizing characteristic, it can be used to kill microorganisms. Through this characteristic of ozone the device for home refrigerator can eliminate germs and odor inside the refrigerator. The refrigerator device can battery powered, or could be powered by the same electrical source that powers the refrigerator.

When the device is operational, the transformer has a voltage output of several thousand volts. One end of the high voltage is connected through wires to a plurality of needles; the other end is connected to a stainless steel mesh and is grounded. With the special feature of the needles of the refrigerator device, a large amount of electrons accumulate at the needles. With such a large voltage difference, the ends of the needles release a large sum of electrical charge flowing towards the stainless steel mesh. During the process, electrons bombard and activate air molecules and consequently create an ionic breeze.

Corona is created at the same time when the needles discharge electrons. The energy generated by the corona break the bonds of oxygen molecules. Then the oxygen atoms recombine to form ozone particles. From this process both ionic breeze and ozone are created. The ionic breeze carries the ozone out of the unit. Since ozone has a high oxidizing characteristic, it can be used to kill microorganisms. This characteristic of ozone can also be utilized to retard the growth of microorganisms and to deodorize. Thus the refrigerator device can fulfill its purposes in eliminating odors and killing bacteria.

Compared to existing technology, this alternative embodiment has the following advantages: (1) it can both deodorize and kill germs; and (2) it can operate automatically and continuously for pre-selected intervals over a long period of time; and (3) it can tolerate wet environments.

While the methods and processes of the present invention have proven to be particularly useful in the area of odor and bacteria management, those skilled in the art can appreciate that the methods and processes can be used in a variety of different applications and in a variety of different areas of manufacture to yield equivalent devices and methods.

These and other features and advantages of the present invention will be set forth or will become more fully apparent in the description that follows and in the appended claims. The features and advantages may be realized and obtained by means of the instruments and combinations particularly pointed out in the appended claims. Furthermore, the features and advantages of the invention may be learned by the practice of the invention or will be obvious from the description, as set forth hereinafter.

BRIEF DESCRIPTION OF THE DRAWINGS

In order that the manner in which the above recited and other features and advantages of the present invention are obtained, a more particular description of the invention will be rendered by reference to specific embodiments thereof, which are illustrated in the appended drawings. Understanding that the drawings depict only typical embodiments of the present invention and are not, therefore, to be considered as limiting the scope of the invention, the present invention will be described and explained with additional specificity and detail through the use of the accompanying drawings in which.

In the Figures, like members are given consistent numbers.

DETAILED DESCRIPTION OF THE INVENTION

The present invention is directed to ozone devices for use in enclosed, uninhabited spaces or containers. These devices serve to reduce or eliminate undesirable odors and bacteria and serve to prolong the shelf life perishable items such as foodstuffs.

Figure 1:
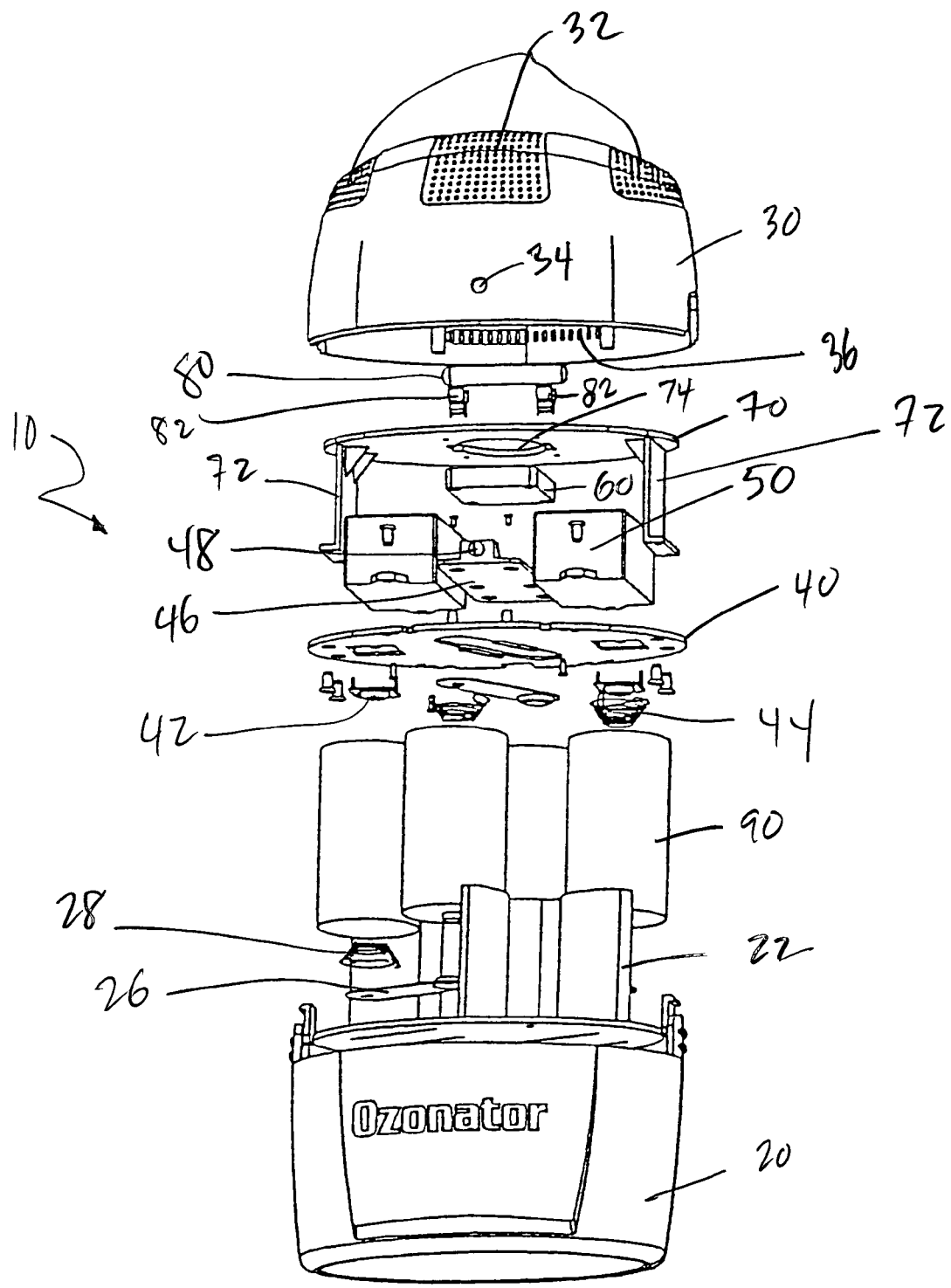
FIG. 1 is a exploded diagram of illustrative components of the present invention.
Figure 2:
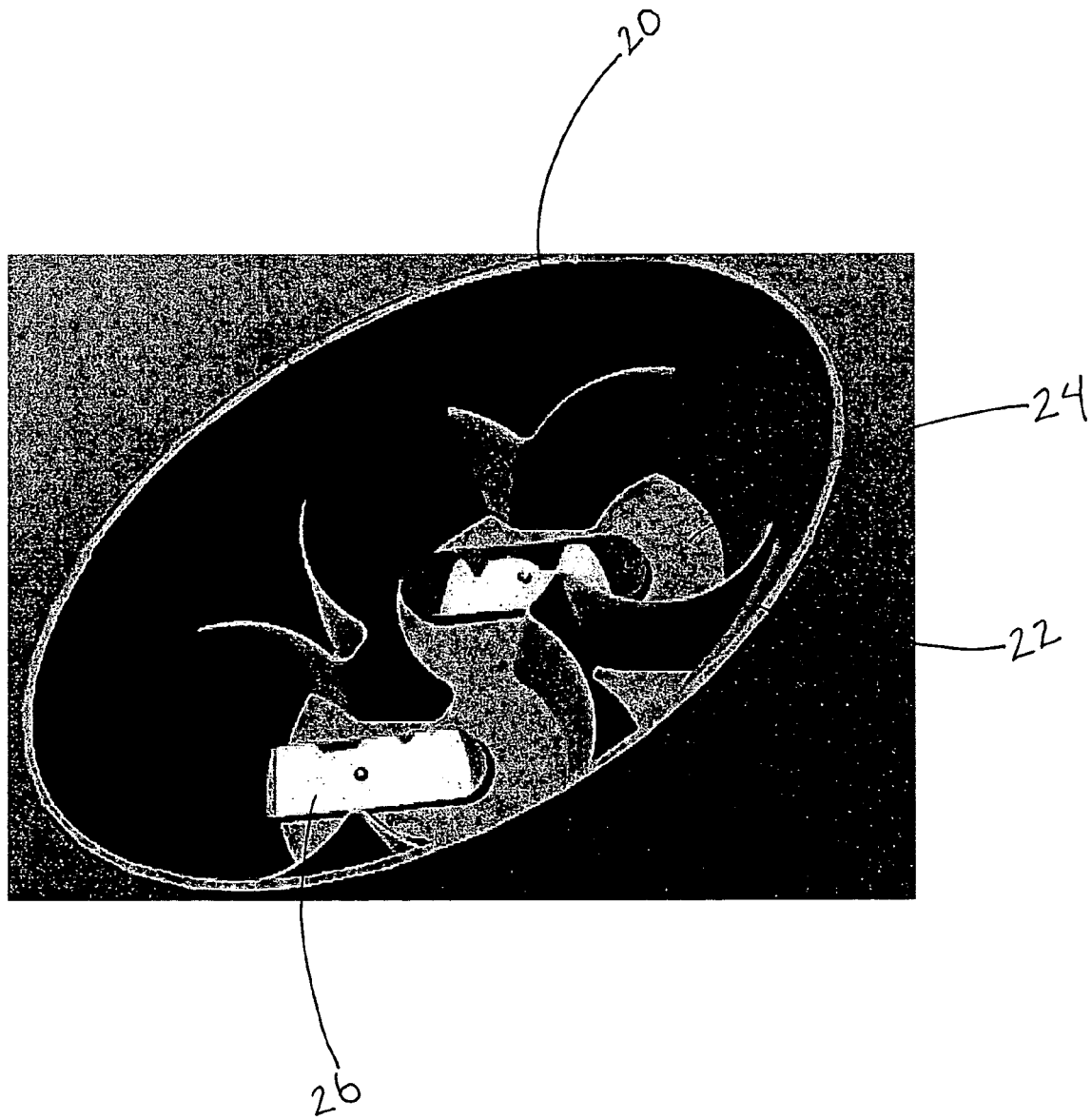
FIG. 2 is an illustrative embodiment of the base or bottom shell of the present invention.
Figure 3:
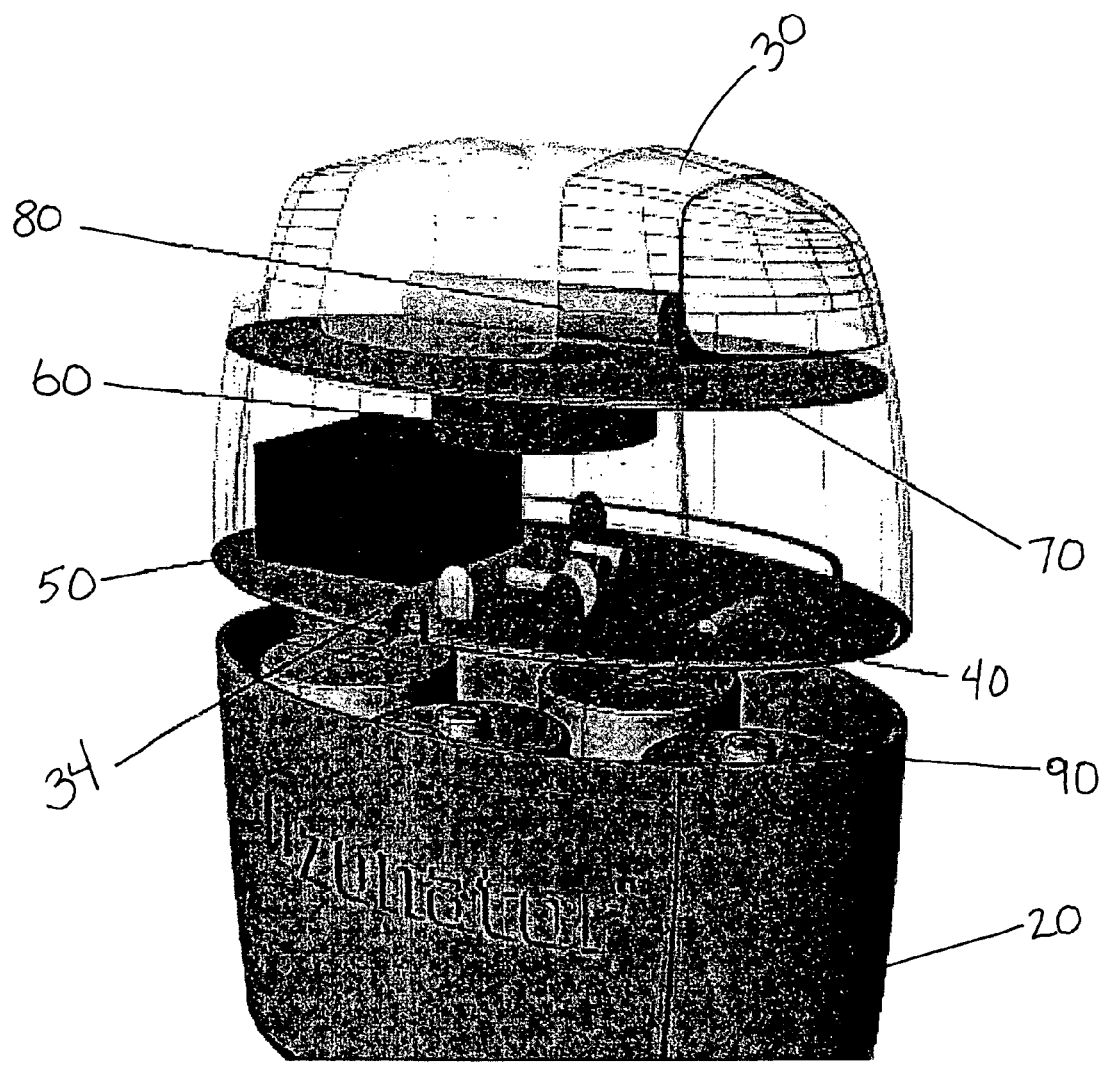
FIG. 3 is an illustrative embodiment of the top cover of the present invention.

As illustrated in FIGS. 1-3, the ozone device 10 of the present invention is comprises bottom shell 20 and top cover 30. Bottom 20 and top 30 mate in a conventional snap-fit configuration. Bottom 20 comprises battery well walls 22 defining battery wells 24. Battery electrical poles 26 are disposed in battery wells 24. In one embodiment, bottom 20 is fabricated in a unitary body so as to be water resistant. In this way, device 10 can sit or stand in a pool of moisture. Batteries used to power the device remain in dry and battery poles 26 are not subject to corrosion from moisture. Conventional battery contact springs 28 may be employed.

Top 30 comprises a covering or housing. Top 30 may be injection molded. A thermoplastic polymer is recommended. Top 30 comprises screened openings 32 through which air and ozone may flow. The screens may be preformed to fill openings in top 30. Top 30 also defines an opening 34 in which LED 48 is disposed to view of the user. Top 30 further defines one or more inlets 36 to permit ambient air to be drawn into device 10 in operation.

Top 30 houses circuit board platform 40. Platform 40 host electrical components and circuitry 46 such as a circuit board to control power, timer-control circuits, ozone generation and air circulation and illumination of LED 48. Platform 40 also hosts corresponding battery poles 42. Again, battery contact springs 44 may be employed. One or more transformers 50, as needed, may be disposed on platform 40.

Top 30 also houses support 70 held a distance away from platform 40 by support legs 72. Support 70 defines aperture 74. Fan 60 is attached to support 70 on one side of aperture 74. In one embodiment, ozone is generated using conventional corona discharge from conventional tubular construction 80 known to those of skill in the art. Tube 80 supported on support 70 by yokes 82. Ozone generation can be accomplished utilizing the mesh/needle structure known in the art and illustrated in FIG. 6. Conventional wiring configurations known to those skilled in the art, not shown, are used to connect the various electrical components.

Fitted together, device 10 may be about six inches tall from top to bottom, about five inches wide from side to side, and about 3 inches deep or thick from front to back.

Figure 4:
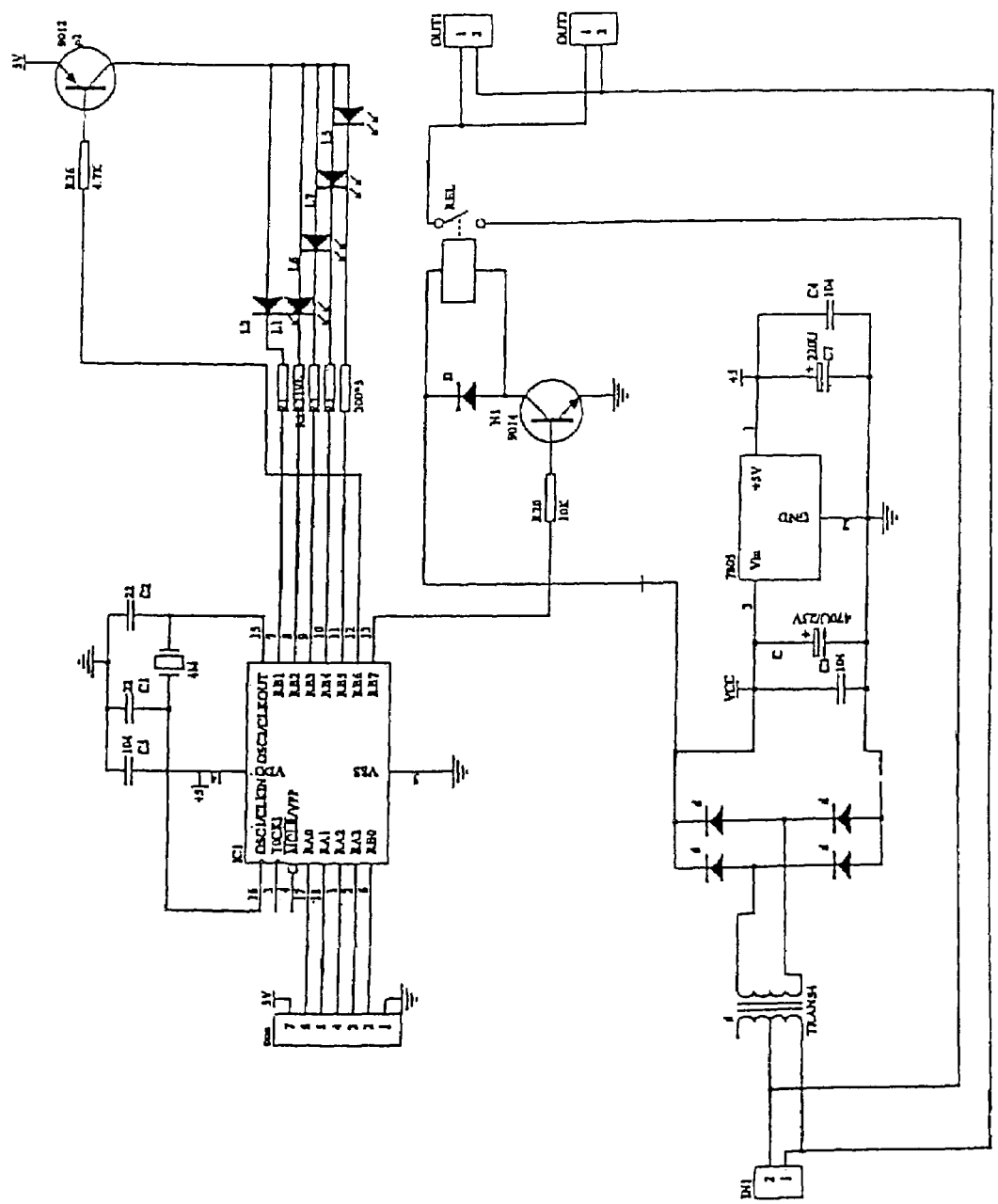
FIG. 4 is an exemplary schematic of electronic components.
Figure 5A:
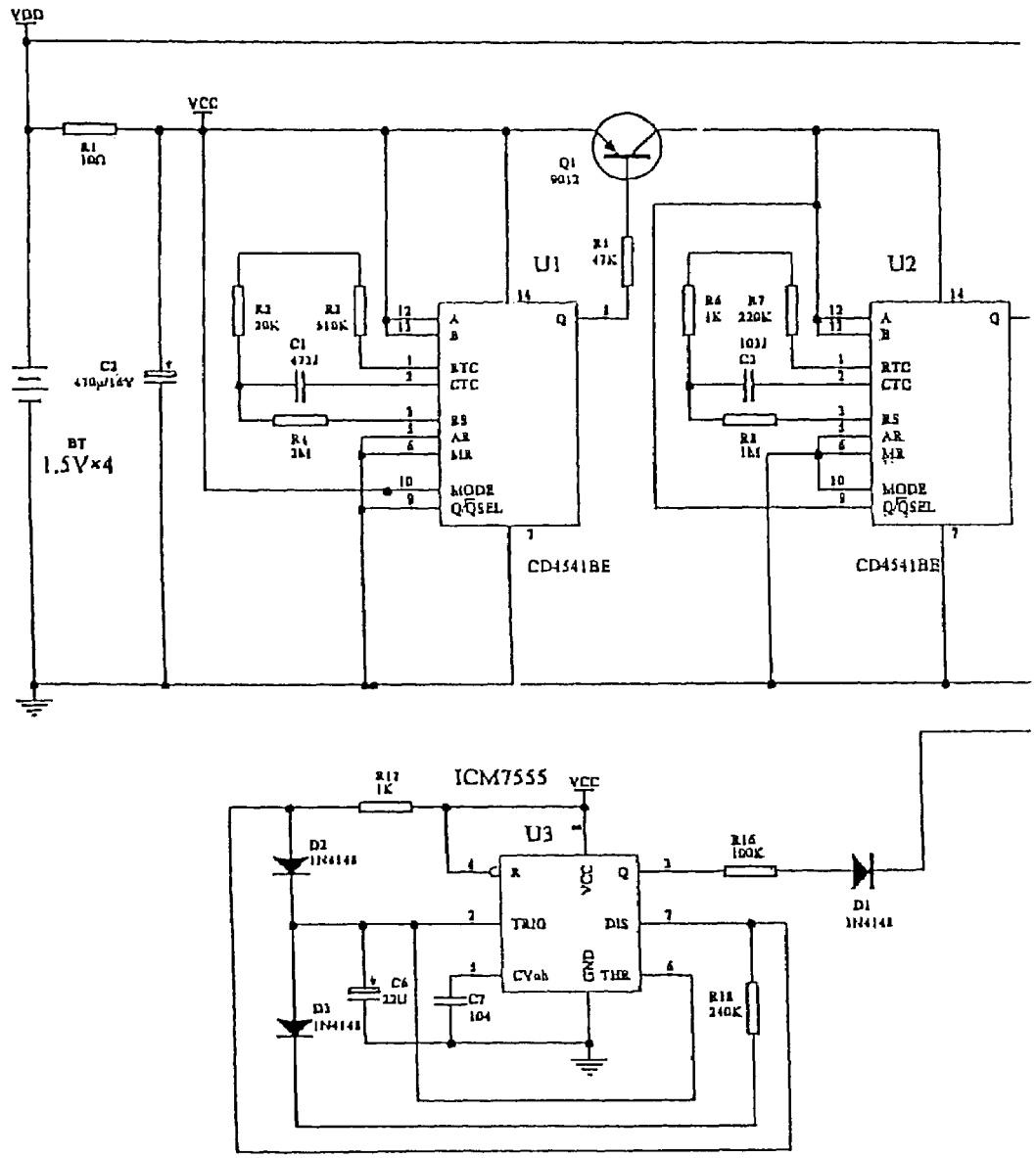
FIG. 5A and 5B are exemplary schematic of electronic components.
Figure 5B:
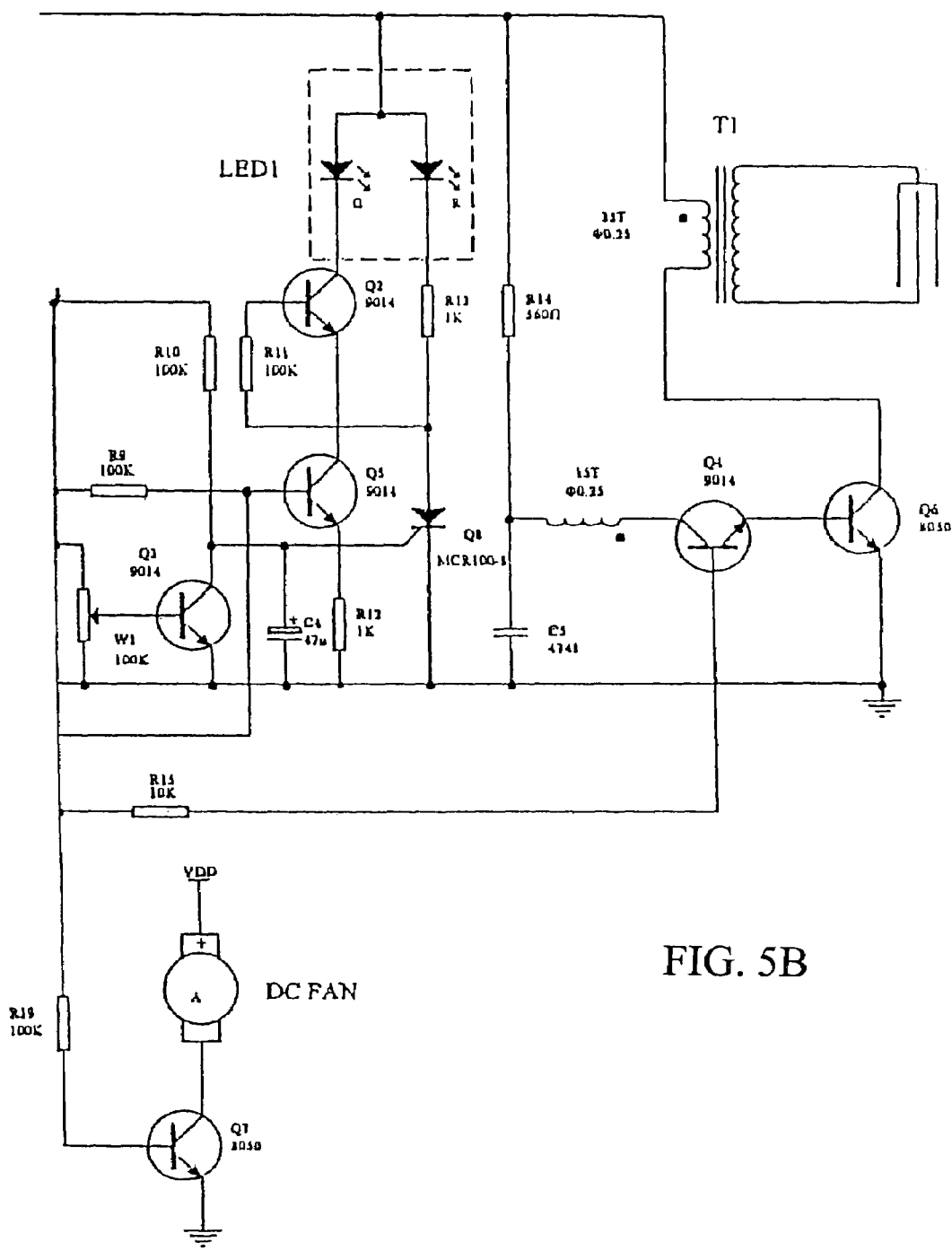

Exemplary electrical diagrams are shown in FIGS. 4 and 5A and 5B.

In operation, device 10 utilizes a plurality of dry batteries 90 as its electrical source. Batteries 90 are placed in battery wells 24. The electrical circuit of the device is activated or closed when top 30 is connected to bottom 20. There are no on-off, hi-lo switches. No user selection as to mode is needed or required. A voltage or high-voltage transformer 50 operates under the direction of a timer-control circuit 100, see FIG. 6. Light-emitting diode (LED) 48 illuminates as controlled.

Transformer 50 can have a high voltage output of several thousand volts. In one embodiment, voltage is connected to the needles 110 and the other end is connected to the stainless steel mesh 120 and is grounded with its electronic circuit. Because of the special feature of the needles 110 having sharp points at the ends and the high voltage difference between the needles 110 and the stainless steel mesh 120, needles 110 accumulate a large amount of electrons and discharge these electrons towards the stainless steel mesh 120 within a certain distance between the needles 110 and the stainless steel mesh 120. During the discharging process of electrons from the needles 110 to the stainless steel mesh 120, the electrons in the air create an ionic breeze. Corona is created at the same time when the needles 110 discharge electrons. The energy generated by the corona generates ozone. From this process both ionic breeze and ozone ($O_3$) are created. The ionic breeze carries the ozone out of the unit.

Figure 6:
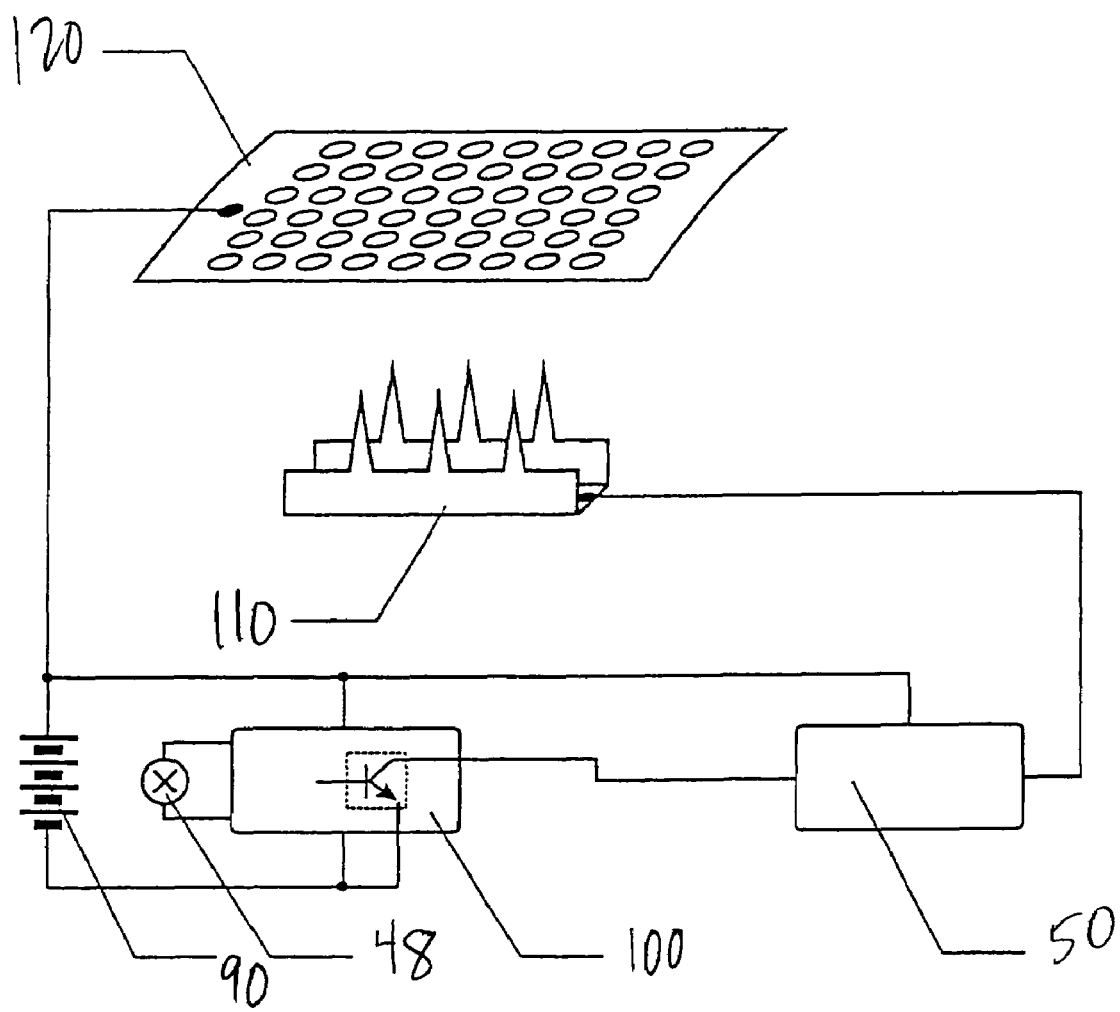
FIG. 6 illustrates a configuration for ozone generation.

As illustrated in FIG. 6, the device has a timer-control circuit 100 that can turn the high-voltage transformer 50 into a standby mode under a certain period of time. When the device is under such a standby mode, the light-emitting diode 48 blinks once every 2.5 seconds on average. The device generally can have high voltage output of between 2,000 to 3,000 volts generated through the high-voltage transformer 50. Needles 110 preferably have sharp points at the ends and are arranged in at least two rows. Mesh 120 generally has the shape of a screen or net. Typically, the distance between needles 110 and stainless steel mesh 120 is generally set within 3 mm to 7 mm. Such a device can be powered by dry batteries 90.

Figure 7:
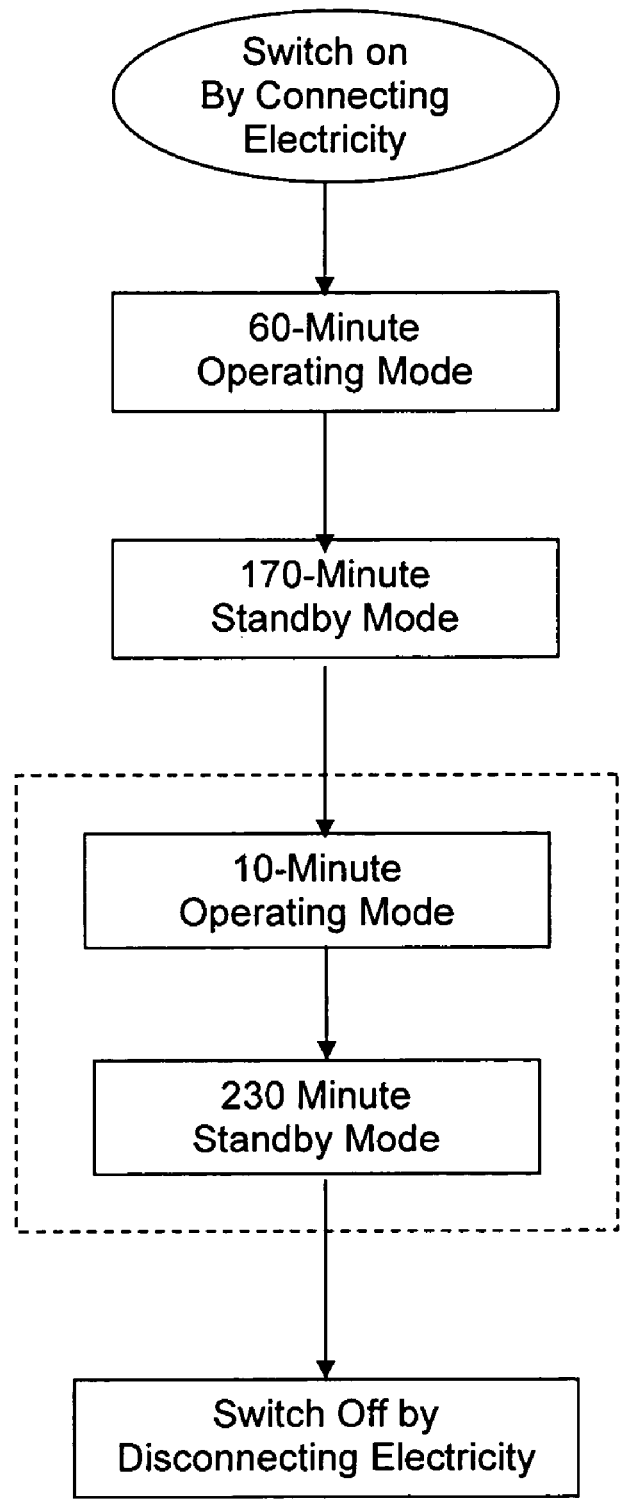
FIG. 7 illustrates an operational mode of the present invention.

In one operational mode, upon initial activation of device 10, it is switched on and can be configured to operate to generate ozone continuously for an hour. After an hour of operation the device will operate for another 10 minutes. Then after the 10 minutes of operating mode the device will be under the first standby mode of 170 minutes. After 170 minutes of the first standby mode the device will operate for 10 minutes. After the 10 minutes of operating mode the device will be under a normal standby mode of 230 minutes. After the 230 minutes of normal standby mode the device will operate for 10 minutes. That is, after the 230 minutes of standby mode the device will be again under an operating mode of 10 minutes. After another 230 minutes of standby mode the unit will then operate automatically in a cycle of 10 minutes operating mode and 230 minutes standby mode until the device is switched off by separating the top cover and the bottom shell. See FIG. 7. Through the automatic operation cycle of the device, ozone concentration level is maintained inside home refrigerator to effectively eliminate odor and bacteria.

Another preferred interval of operation is to have device 10 generate ozone for two minutes in fifty minute intervals.

In another operational mode, the device may operate over a range of times. For example, the ozone generation cycles may ranges from about 8 minutes to about 12 minutes and have standby cycles ranging from about 210 to about 250 minutes during the automatic operation cycle.

As device 10 generates an ionic breeze and ozone, fan 60 draws air into top 30 and blows through aperture 72 to circulate ozone out of top 30 through screened openings 32.

Because ozone has a high oxidizing characteristic, it can be used to kill microorganisms. This characteristic of ozone can also be utilized to retard the growth of microorganisms and to deodorize. Thus the embodiment for home refrigerator use can fulfill its purposes in eliminating odors and killing bacteria.

If desired, device 10 can be outfitted with an ozone monitor and corresponding electronic circuitry to activate ozone generation to maintain a pre-selected level of ozone in the confined space.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

The invention claimed is:

1. An apparatus for use in a home refrigerator comprising:
    a submersible and waterproof unitary bottom shell for housing batteries and keeping batteries dry when the bottom shell is submersed in water,
    a top cover;
    means for generating ozone disposed in the top cover; and
    time-control circuitry also disposed in the top cover, the time-control circuitry adapted to automatically control durations of periods of generation of ozone and intermittent standby periods.

2. The apparatus of claim 1 wherein the bottom shell and top cover are constructed of plastic and fit together in snap-fit configuration.

3. The apparatus of claim 1 further comprising a high-voltage transformer, wherein the high-voltage transformer produces a voltage output from about 2,000 volts to about 3,000 volts.

4. The apparatus of claim 1 wherein the means for generating ozone comprises needles having sharp points at the ends and an arrangement of needles comprises at least two rows.

5. The apparatus of claim 1 wherein the means for generating ozone further comprises a steel mesh configured as a screen or net.

6. The apparatus of claim 1 wherein the means for generating ozone generates ozone for about 8 to about 12 minutes and has a standby cycle in which no ozone is generated for a period of time from about 210 to about 250 minutes during the automatic operation of the apparatus.

7. The apparatus of claim 1 wherein the means for generating ozone generates ozone for two minutes with fifty minutes standby period between ozone generation.

8. The apparatus of claim 1 further comprising waterproofed electrical components housed in said apparatus.

9. The apparatus of claim 1 further comprising an ozone monitor that maintains a pre-selected level of ozone.

10. A method for deodorizing the inside of a home size refrigerator comprising the steps:
    obtaining a submersible and waterproof unitary bottom shell for housing batteries and keeping batteries dry when the bottom shell is submersed in water,
    obtaining a top cover;
    obtaining means for generating ozone disposed in the top cover;
    obtaining a time-control circuitry also disposed in the top cover, the time-control circuitry adapted to automatically control durations of periods of generation of ozone and intermittent standby periods; and automatically generating ozone for pre-selected cycle of time.

11. The method of claim 10 wherein the ozone generating cycle comprising:
  generating ozone inside the refrigerator for a period of time from about 8 minutes to about 12 minutes and providing a standby cycle in which the generation of ozone is discontinued for a period of time from about 210 minutes to about 250 minutes, and automatically repeating the ozone generating and standby cycles.

12. The method of claim 10 wherein the ozone generating cycle comprising:
  generating ozone inside the refrigerator for a period of time for about two minutes with fifty minute intervening standby periods.

13. The method of claim 10 wherein the method further comprises reducing the rate of food decomposition by flowing ozone over the food.

14. The method of claim 10 further comprising waterproofing said electrical circuitry.

15. The method of claim 10 further comprising obtaining an ozone monitor disposed in the top cover that maintains a pre-selected level of ozone.

* * * * *